US006818907B2

(12) United States Patent
Stark

(10) Patent No.: US 6,818,907 B2
(45) Date of Patent: Nov. 16, 2004

(54) SURFACE PLASMON ENHANCED ILLUMINATION SYSTEM

(75) Inventor: Peter Randolph Hazard Stark, Andover, MA (US)

(73) Assignee: The President and Fellows of Harvard College, Boston, MA (US)

( * ) Notice: Subject to any disclaimer, the term of this patent is extended or adjusted under 35 U.S.C. 154(b) by 66 days.

(21) Appl. No.: 09/981,280

(22) Filed: Oct. 16, 2001

(65) Prior Publication Data

US 2002/0056816 A1 May 16, 2002

Related U.S. Application Data

(60) Provisional application No. 60/312,214, filed on Aug. 14, 2001, provisional application No. 60/293,153, filed on May 23, 2001, and provisional application No. 60/240,886, filed on Oct. 17, 2000.

(51) Int. Cl.[7] .................................................. G02F 1/03
(52) U.S. Cl. ..................... 250/492.1; 250/216; 250/306
(58) Field of Search ............................. 250/492.1, 216, 250/306, 307, 310, 311; 359/245

(56) References Cited

U.S. PATENT DOCUMENTS

| | | | |
|---|---|---|---|
| 5,973,316 A | | 10/1999 | Ebbesen et al. |
| 6,040,936 A | * | 3/2000 | Kim et al. .................. 359/245 |
| 6,052,238 A | | 4/2000 | Ebbesen et al. |
| 6,236,033 B1 | | 5/2001 | Ebbesen et al. |
| 6,285,020 B1 | | 9/2001 | Kim et al. |
| 6,441,298 B1 | * | 8/2002 | Thio .......................... 136/250 |

OTHER PUBLICATIONS

Ebbesen, T. W., Lezec, H. J., Ghaemi, H. F., Thio, T. & Wolff, P. A. Extraordinary optical transmission through sub–wavelength hole arrays. Nature 391, 667–669 (1998).

Ghaemi, H. F., Thio, T., Grupp, D. E., Ebbessen, T. W. & Lezec, H. J. Surface plasmons enhance optical transmission through subwavelength holes. Phys. Rev. B 58, 6779–6782 (1998).

Kim, T. J., Thio, T., Ebbessen, T. W., Grupp, D. E. & Lezec, H. J. Control of optical transmission through metals perforated with subwavelength hole arrays. Opt. Lett. 24, 256–258 (1999).

(List continued on next page.)

*Primary Examiner*—Nikita Wells
*Assistant Examiner*—Anthony Quash
(74) *Attorney, Agent, or Firm*—Charles G. Call

(57) ABSTRACT

Methods and apparatus for producing small, bright nanometric light sources from apertures that are smaller than the wavelength of the emitted light. Light is directed at a surface layer of metal onto a light barrier structure that includes one or more apertures each of which directs a small spot of light onto a target. The incident light excites surface plasmons (electron density fluctuations) in the top metal surface layer and this energy couples through the apertures to the opposing surface where it is emitted as light from the apertures or from the rims of the apertures. Means are employed to prevent or severely limit the extent to which surface plasmons are induced on the surface at the aperture exit, thereby constraining the resulting emissions to small target areas. The resulting small spot illumination may be used to increase the resolution of microscopes and photolithographic processes, and to increase the storage capacity and performance of optical data storage systems.

23 Claims, 5 Drawing Sheets

OTHER PUBLICATIONS

Grupp, D. E., Lezec, H. J., Ebbessen, T. W., Pellerin, K. M. & Thio, T. Crucial role of metal surface in enhance transmission through subwavelength apertures. App. Phys. Lett. 77, 1569–1571 (2000).

Sönnichsen, C., Duch, A. C., Steininger, G., Koch, M. & Plessen, G. V. Launching surface plasmons into nanoholes in metal films. App. Phys. Lett. 76, 140–142 (2000).

Sandoz, P., Giust, R. & Tribillon, G. Multi–aperture optical head for parallel scanning near field optical microscopy. Opt. Commun. 161, 197–202 (1999).

Grupp, D. E., Lezec, H. J., Thio, T. & Ebbessen, T. W. Beyond the Behte Limit: Tunable Enhanced Light transmission Through a Single Sub–Wavelength Aperture. Adv. Mater. 11, 860–862 (1999).

Strelniker, Y. M. & Bergman, D. Optical transmission through metal films with subwavelength hole array in the presence of a magnetic field. Phys. Rev. B 59, 12763–12766 (1999).

Raether, H. Surface Plasmons on Smooth and Rough Surfaces and on gratings (Springer–Verlag, 1988).

Lezec, H. J. et al. Beaming light from a subwavelength aperture. Science 297, 820–822 (2002).

Jung, L.S., Campbell, C.T., Chinowsky, TM, Mar, M.N. & Yee, S.S. Quantitative Interpretation of the Response of Surface Plasmon Resonance Sensors to Adsorbed Films. Langmuir, vol. 14, No. 19, 5636–5648 (1998).

Thio, T., Pellerin, K.M. & Linke, R.A. Enhanced light transmission through a single subwavelength aperture. Optics Letters, vol. 26, No. 24, 1972–1974(2001).

* cited by examiner

SURFACE PLASMON ENHANCED ILLUMINATION SYSTEM

CROSS REFERENCE TO RELATED APPLICATIONS

This application claims the benefit of the filing date of U.S. Provisional Application Ser. No. 60/240,886 filed on Oct. 17, 2000, further claims the benefit of the filing date of U.S. Provisional Application Ser. No. 60/293,153 filed on May 23, 2001, and further claims the benefit of the filing date of a U.S. Provisional Application Ser. No. 60/312,214 filed on Aug. 14, 2001.

FIELD OF THE INVENTION

This invention relates to methods and apparatus in which target areas are illuminated with an array of spots or lines of light having very small dimensions.

BACKGROUND OF THE INVENTION

Typical optical microscopy, far-field light microscopy, cannot resolve distances less than the Rayleigh limit. The Rayleigh criterion states that two images are regarded as just resolved when the principal maximum (of the Fraunhofer diffraction pattern) of one coincides with the first minimum of the other [see Born, M. and Wolf, E. *Principles of Optics*. Cambridge University Press $6^{th}$ ed. p.415 (1980)]. For a circular aperture, this occurs at $$w = 0.61 \frac{\lambda}{NA}$$

For example, the wavelength ($\lambda$) at the peak emission of a green fluorescent protein (EGFP) is 508 nm. Hence, for a very high numerical aperture (NA) of the objective, NA of 1.4, the minimum separation (w) that can be resolved in a GFP labeled sample is 221 nm. Currently, there are several possible methods for achieving resolution of spatial locations of proteins below the Rayleigh limit. They include: Confocal Microscopy, Fluorescence Resonance Energy Transfer (FRET), Atomic Force Microscopy (AFM), Near-Field Scanning Optical Microscopy (NSOM), Harmonic Excitation Light-Microscopy (HELM), Stimulated Emission Depletion Microscopy (STED-Microscopy) and Electron Microscope Immunocytochemistry.

Confocal Microscopy is a technique in which a very small aperture(s) is/are placed in the optical path to eliminate any unfocused light. This allows for a substantial increase in signal to noise ratio over conventional light microscopy. Also, it is possible to reduce the width of the central maximum of the Fraunhoffer pattern using a small slit or aperture. This, in turn allows a substantially enhanced resolution of 1.4 times better than the Rayleigh limit. Therefore, with this method, using the above protein as an example, a spatial resolution of 156 nm is achieved.

Typical confocal microscopy is not without disadvantages. By increasing the signal to noise ratio by decreasing the aperture size, the total signal level decreases concurrently. To bring the signal back to a useful level, the input power level must be increased. This, in turn, not only can cause photo-bleaching in the fluorophores at which one intends to look but also the surrounding area where the light is incident, just not collected. A method around this is to use two-photon excitation. Fluorescence from the two-photon effect depends on the square of the incident light intensity, which in turn, decreases approximately as the square of the distance from the focus. Because of this highly nonlinear (~fourth power) behavior, only those dye molecules very near the focus of the beam are excited, while the surrounding material is bombarded only by comparatively much fewer of the low energy photons, which are not of enough energy to cause photo bleaching. Multi-photon excitation requires highly skilled technicians and is somewhat expensive for clinical use. Because it acquires only a small area at once, the surface must be scanned in three dimensions for mapping.

Fluorescence Resonance Energy Transfer (FRET) can provide exquisite resolution of single chromophores. The resonance occurs when one fluorophore in an excited state transfers a portion of its energy to a neighboring chromophore. For this to take place, there must exist some overlap between the emission spectrum of the fluorophore to absorption spectrum of the chromophore (the frequency of the emission spectrum should be somewhat higher than the absorption spectrum of the chromophore). The process does not occur through photonic emission and absorption but through a dipole-dipole interaction. The strength of the interaction varies as $r^{-6}$. The Forster distance [see Forster, T Discuss. *Faraday Soc.* 27 7–29 (1959)] is the distance at which the efficiency of the transfer is such that there exists equal probability that the fluorophore loses energy to radiative decay or dipole-dipole interaction. The Forster distance, essentially, is the threshold at which FRET will no longer exist for a given pair. Typically the Forster distance is between 3 and 6 nm [see Pollok & Heim "Using GFP in FRET-based Applications" *Trends in Cell Biology* 9 pp57–60 (1999)].

By placing either of the complementary pair near the other, resolutions of less than the Forster distance can be attained. The problem with this technique in determining relative locations is that one of the pair needs to be located within the resolution tolerances desired for spatial mapping. This can be achieved by placing one of the pair on a probe used in either atomic force microscopy (AFM) or near-field scanning optical microscopy (NSOM). Another problem is that dipole-dipole interactions are dependent on the relative orientation of the two. To maximize signal from the interaction would require a 3D scan around one of the pair.

Atomic Force Microscopy (AFM) can be envisioned as a very small (usually metal) stylus dragged across a surface giving feedback as to the height, Z, of the stylus relative to the surface. Resolution can be as fine as the scanning step size (typically 5 nm). By scanning across the surface, X and Y coordinates are obtained provided that the origin remains fixed (i.e., that there is no drift in the translation stage due to thermal or other effects). There are many methods for ensuring that the stylus does not actually contact the sample but maintains very accurate resolution of the Z coordinate. Because only surface morphology is measured, differentiating several molecules can be extremely difficult unless the dimensions and orientations of those molecules are well known. A solution to this might be to add tags of discrete lengths or shapes, which could be bound indirectly to the molecules of interest. This method, however, would require that the tissue sample to be planar before the tags were bound to the surface.

To increase the information of AFM, one could use Near-Field Scanning Optical Microscopy (NSOM or SNOM). NSOM uses a principle similar to AFM in which a stylus is scanned over a surface providing topographical information. However, the stylus is a conductor of photons. By emitting light from the tip of the stylus, optical measurements such as fluorescence can be obtained. Most often, these styli are fiber probes that have tapered tips and then are plated with a conductive material (aluminum is most often chosen as its skin depth for optical radiation is quite low, ~13 nm at 500 nm) with a small aperture where the coating is broken. [See Betzig & Trautman "Near-Field Optics: Microscopy, Spectroscopy, and Surface Modification beyond the Diffraction Limit" *Science* 257 pp189–195 (1992)]. Another approach is to use what are called "apertureless probes" [see Sanchez, Novotny and Xie "Near-Field Fluorescence Microscopy Based on Two-Photon Excitation with Metal Tips" *Physical Review Letters* Vol 82 20 pp 4014–4017 (1999)] where an evanescent wave is excited by bombardment with photons at the tip of a sharpened metal probe. Because the tip can be made very sharp (radii of 5 nm are achievable), resolutions can be correspondingly smaller. An associated problem with the "apertureless probes" is that the probe generates a white light continuum, which significantly decreases the signal to noise ratio.

By making the diameter (assuming a circular geometry) of the emission portion of the tip of the stylus very small (smaller than resolution desired) and keeping the tip to sample distance less than that distance, so that the diffraction is small, a nanometric light source is available. This light source can be used to excite fluorescence in the sample. Because the size of the source is very small and the scanning increments are also very small, highly resolved information on spatial locations of the fluorophores can be gleaned by inspection in the far field. Alternatively, the probe can be used for collection, measuring fluorescence or reflection or even transmission from illumination from the other side of the sample.

Because the aperture size in a conventional probe is so much smaller than the wavelength of the excitation light and only an evanescent mode is supported resulting in very little light is transmitted through the aperture. Diffraction effects limit the effective collimated length from the aperture to less than diameter of the aperture. This, then, requires that the aperture be held below a maximum height above the surface of the sample. Ideally, a fixed height above the surface (usually less than 10 nm) is used for relative contrast measurements. The height of the aperture relative to the surface is kept constant by measuring the shear force on the tip of the probe or by optical methods and is modulated to maintain that height. For this reason, NSOM is particularly susceptible to vibrations and experimental work requires isolation platforms.

Scanning the surface takes a fair amount of time. Thermal drift in commercially available open and closed loop nanometric scanning stages is about 20–30 nm/min. [see Frohn, Knapp and Stemmer "True optical resolution beyond the Rayleigh limit achieved by standing wave illumination" *Proceedings of the National Academies of Science* Vol. 97, 13 pp 7232–7236 (2000)]. This can be severely limiting if scanning time is more than a few tens of seconds and resolution less than 50 nm is desired. If the surface is scanned for several different types of molecules, the required time to investigate a single cell becomes far too large for use in a clinical setting and would require multiple homings of the scanning stage. An approach to diminishing the scanning time may be to scan with multiple probes concurrently. This approach would be limited to just a few probes as on a small ($20^2$ $\mu m^2$) surface, the relatively large size of the probes' bodies would interfere mechanically with each other.

U.S. Pat. Nos. 5,973,316 and 6,052,238 issued to Ebbesen et al. of the NEC Research Institute, Inc. describe a NSOM device which employs an array of subwavelength apertures in a metallic film or thin metallic plate. Enhanced transmission through the apertures of the array is greater than the unit transmission of a single aperture and is believed to be due to the active participation of the metal film in which the aperture array is formed. In addition to enhancing transmission, the array of apertures reduces scanning time by increasing the number of nanometric light sources.

A second method for increasing the number of light sources illuminates the sample with a mesh-like interference pattern and by post processing of the images. In Harmonic Excitation Light Microscopy (HELM), a laser is split into four beams and two of those beams modulated to produce an extended two-dimensional interference field with closely spaced antinodes. By introducing the beams at an angle to the surface to be imaged, an effective offset in reciprocal space is produced around an origin. If four images are taken around this origin and one at the origin, it is possible to construct, with post processing, a smaller single antinode which acts as a nanometric light source. This process can result in a lateral resolving power of close to 100 nm or half of the Rayleigh distance for green light. Because only a few images are required to map an entire surface, the acquisition time is extremely short (around 1.6 s for a 25 $\mu$m×25 $\mu$m area with 100 nm resolution.) Due to the required precision in the location of the four images around the origin and the drift associated with the scanning stage, it is unlikely that the resolution will be dramatically increased.

Another new form of microscopy is that introduced by Klar et al. [see Klar, Jakobs, Dyba, Egner and Hell "Fluorescence microscopy with diffraction resolution barrier" *Proceedings of the National Academies of Science* Vol 97 15 pp 8206–8210 (2000)] called Stimulated Emission Depletion (STED) Microscopy. STED microscopy is based on a method of quenching fluorescence by stimulated emission depletion reducing the fluorescing spot size. [See Hell & Wichmann "Breaking the Diffraction Resolution Limit by Stimulated-Emission-Depletion Fluorescence Microscopy" *Opt. Lett* 19 11 780–782 (1994); Lakowicz, Gryczynski, Bogdanov and Kusba. "Light Quenching and Fluorescence Depolarization of Rhodamine-B and Applications of this Phenomenon to Biophysics" *J. Phys. Chem.* 98 1 334–342 (1994); Hell, S. W. *Topics in Fluorescence Spectroscopy*, ed. Lakowicz (Plenum Press, NY), Vol. 5, pp. 361–422; and Klar & Hell "Subdiffraction resolution in far-field fluorescence microscopy" *Opt. Lett* 24 14, 954–956 (1999)]. Fluorescence can be quenched by subjecting a fluorophore to light at the lower energy edge (red side) of its emission spectrum. This forces the fluorophore to a higher vibrational level of the ground state, which, by decay of that state prevents re-excitation. Fluorescence can be turned on, with an ordinary excitation source, and turned off, with the STED beam, at will. By introducing an interference pattern in the STED beam, a local set of maxima and minima can be created. If the maxima of the STED beam are overlaid onto the fluorescence induced by the excitation beam, the fluorescence is quenched. However, where the minima occur, fluorescence continues. The fluorescing spot size is controlled by the union of the minimum or minima of the STED beam and the maximum of the excitation beam. Because STED is nonlinear with intensity, the sharpness of the minimum, maximum transition can be effectively increased allowing a narrow, almost delta behavior to be displayed. This, however, can result in severe photo stress to the sample and, possibly, dual photon effects, causing competing modes in the area where quenching is desired. So far, resolution in the radial (X, Y) direction is around 100 nm, but there is no reason to expect that the resolution can't be substantially improved. Once again, though, STED microscopy is a scanning type and will suffer from the same drawbacks all scanning instruments do, (e.g., thermal drift, vibration problems, registration of near field excitement with far field collection and scan time.)

SUMMARY OF THE INVENTION

The present invention contemplates a different technique to achieve sub-Rayleigh criterion resolution, which is here called "Surface Plasmon Enhanced Illumination" (SPEI). SPEI is related to NSOM in that multiple nanometric light sources are created by subwavelength apertures. By applying the principles of the present invention, a significant reduction in the size of the area illuminated by each aperture is achieved, resulting in significantly improved resolution.

The present invention takes the form of methods and apparatus that employ novel physical structures to provide nanometric spot or line illumination. In accordance with the invention, one or more apertures are formed through a first planar conductive material. Each aperture (which may be either a hole or a slit) has at least one cross-sectional dimension which is less than the wavelength of light which is incident to the planar material. In accordance with a feature of the invention, the structure includes means for confining the electronic excitation induced in that portion of the planar surface near the end of the aperture from which the light exits.

The conductive plane that receives the incident light may be placed on one outer surface of a dielectric material through which the aperture passes. The dielectric material prevents excitation of large densities of surface plasmons from being induced in an exposed conductive surface adjacent to the aperture opening where the light exits the structure.

Alternatively, the sidewalls of the aperture may be conductive to conduct excitation currents and act as a pseudo-waveguide for the light traveling through the aperture. At the exit end of the aperture, the amount of exposed conductive material is limited to an area immediately surrounding the hole exit by a dielectric material, or by a groove cut into the surface of the conductive material at the exit plane to a depth at least equal to the skin depth of the induced excitation and of such width and spacing to prevent an unwanted resonance of surface plasmons in that surface.

Alternatively, the conductive plane that receives the incident light may take the form of a "good metal" layer with a "bad metal" layer having significantly different dielectric properties being sandwiched between the good metal layer and a dielectric substrate. The bad metal layer is preferably opaque to the light to be emitted from the surface of the good metal and its resonance (as determined by its dielectric function, the surface roughness and the dielectric functions of the materials on either side of the bad metal layer) should be very different from the resonance of the "good" metal, such that at desired frequency, light transmitted is emitted only from the holes and not from the exit surface of the array. The insulating dielectric substrate ensures that there can be no surface plasmon excitation from the good metal layer through the light barrier. When a bad metal layer is used that is both opaque to light and has sufficiently different dielectric properties relative to the good metal to eliminate resonant coupling, the dielectric insulator may be eliminated.

The present invention substantially reduces, compared to an array of subwavelength apertures in a monometallic film such as those described by Ebbesen et al., the size of the area of illumination produced by each aperture using the combination of a metallic layer on which surface plasmons are induced by incident light and surface composed of a material of substantially different dielectric function, such as an insulator or a different metal, so that the excitation of the surface plasmons in the light emitting surface in the exit surface layer will be different than those excited in the metallic layer that is excited by the incident light, and only the light from the decaying resonant surface plasmons of the exit layer will emit from that surface. The photons associated with the resonance of the incident or upper surface will be constrained to exit from the hole itself or from the walls of the hole.

In accordance with the invention, the light barrier comprises an illuminated surface consisting of a continuous conductive metallic layer in combination with an exit layer having substantially different dielectric properties. One or more apertures through the barrier (one or more holes or slits) then form "photonic funnels" through the barrier.

The invention may advantageously take the form of an array of apertures (holes or slits) formed in structure consisting of a dielectric substrate coated with a conductive metal film on one or both surfaces, or by a thick metallic film, and which further incorporates means for confining the electronic surface excitation to an area immediately adjacent to the apertures where light exits the structure. The means for confining the electronic surface excitation preferably takes the form of a layer of material having dielectric properties that differ substantially from those of the illuminated metal layer, and may consist of a dielectric insulator, a "bad metal" having different dielectric properties, grooves or surface irregularities at the exit surface, or a combination of these. The structure which confines the electronic surface excitation restricts the size of the spot or line of illumination from each aperture, and the use of an array of aperatures, or an array of surface irregularities on the metal film, increases the intensity of the illumination from each aperture The present invention may also be applied to advantage in an optical data storage device. Several arrangements may be devised for combining the hole array with some medium for data storage. A light source, such as a laser, may be directed onto the front surface of the hole array which collects and funnels the array of light onto an optical storage medium. The bit value stored at each position in the storage medium controls the propagation of light through the storage medium to an adjacent pixel position in a charge coupled device (CCD) or other area detectors. A translation mechanism effects movement of the storage medium relative to the hole array in incremental steps, with each step distance being equal to the aperture size. In an alternative arrangement, data may be represented by illumination levels, such as gray scale values or color levels, and optical means may be used in place of or to supplement the mechanical translation mechanism.

The well defined and highly concentrated areas of illumination created by using such a structure as a light source provide significant advantages in microscopy and in optical data storage devices. The confined illumination patterns produced in accordance with the invention may be used to construct a "Surface Plasmon Enhanced Microscope" (SPEM) exhibiting markedly improved resolution, to construct an optical data storage device capable of storing larger amounts of data in optical storage media with much higher data access rates than is achievable with current optical data storage devices, and to provide a high throughput photolithography technique that can be applied to advantage in semiconductor fabrication and patterning for self-assembly and biological applications.

These and other objects, features and advantages of the present invention may be better understood by considering the following detailed description of specific embodiments of the invention. In the course of this description, reference will frequently be made to the attached drawings.

DETAILED DESCRIPTION

As described in U.S. Pat. Nos. 5,973,316 and 6,052,238 issued to Ebbesen et al., enhanced light transmission occurs through an array of apertures in a metal film due to the surface plasmons induced in the conductive film by the incident light.

Figure 1:
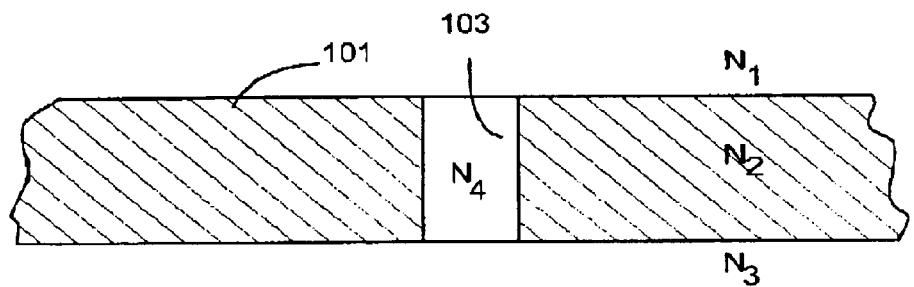
FIG. 1 is a cross-sectional view of a metallic film which is substantially thicker than the skin depth within which optically induced electronic excitation occurs, and through which an aperture having a diameter less than the wavelength of the incident light penetrates.
Figure 2:
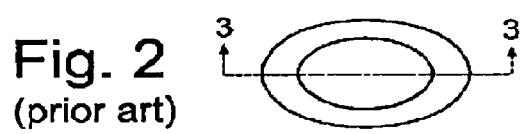
FIG. 2 is a view illustrating the approximate size of the oblong-shaped area illuminated by the light transmitted through the aperture in the film shown in FIG. 1.

FIG. 1 shows a cross section of an optically thick metal film 101. The term "optically thick" means that the thickness of the film 101 is greater than two times the skin depth. For all essential purposes, this means that there is no direct coupling of the surface plasmons (coherent collective excitations of electrons) at the upper surface (the interface between media of index $N_1$ and $N_2$) and the lower surface (the interface between media of index $N_3$ and $N_2$). In a typical case, the indices $N_1$, $N_3$, and $N_4$ are equal while $N_2$, the index of the metal film 101, is substantially different and the metal film 101, unlike the surrounding material, is a conductor of electronic charges.

If the array spacing and the dielectric functions and thickness of the metals and substrates is tailored to attain a high transmission, a significantly higher power density than that transmitted through NSOM (a ratio of about 4000 per aperture for a 50 nm holes) can be delivered through the apertures. This substantially increases the signal to noise ratio of surface plasmon enhanced microscopy (SPEM) over the NSOM at normal resolutions and is allows a smaller hole size to be used, providing better resolution and dramatically decreasing the dwell time required for an adequate signal to be received.

Unfortunately, the coupling (indirect or direct) between the surfaces of the film 101 seen in FIG. 1 have effects that adversely affect desired resolution. Sönnichsen et al., "Launching surface plasmons into nanoholes in metal films", *App. Phys. Lett.* 76, 140–142 (2000) show that, when gold, silver or aluminum films are struck with plane polarized light, surface plasmons are induced in the direction of the polarization. When the plasmons encounter a hole, the coupling to the other side results in light emitted in a prolate shape of a major dimension of about an order of magnitude larger than the hole size. The prolate shape is caused by the radiative decay of the surface plasmons and is a function of the dielectric function of the metal and the wavelength of the incident light and if significant surface roughness exists, the distance between the elements of roughness on that plane.

With a simple isotropic periodically perforated metal film, two potential problems are encountered. First, for use in a microscope and other applications (e.g. optical data storage and photolithography) where small sources of light (high resolution) are required, the existence of the associated prolate pattern diminishes resolution in one dimension severely. Second, the array spacing would have to be such that patterns did not interfere or overlap. Achieving the appropriate spacing would in turn cause the wavelengths at which the surface plasmons are resonant to be shifted, resulting in resonant wavelengths of lower energy. For the excitation of commonly available fluorophores, multi-photon (probably three or four) excitation would be required. Of course, the prolate pattern could simply be accepted and the resolution in the direction of the polarization (along the major axis of the pattern) would default to that dictated by the Rayleigh criterion for that wavelength and numerical aperture.

If a smaller spot illumination size (a nanometric light source) is required, the prolate shape generated from the geometry shown in FIG. 1 is undesirable. If the incident light is polarized, the long dimension of the pattern shape is probably only loosely dependent on the hole size and more dependent on the surface roughness, since rougher surfaces act as very small antennae, which cause SPs to decay, spatially, more rapidly than would be the case if the film surface were smooth. Moreover, the frequency of the light will also affect the pattern shape. Note also that the preferred shape of the intensity pattern for spot illumination should exhibit a step function rather than the extended somewhat gaussian pattern that is seen along the major axis of the prolate shape. In accordance with the present invention, novel structures are used to minimize or eliminate the prolate pattern described above. If the emitting surface (bottom) is no longer continuous but is instead constructed to constrain the propagation of surface plasmons to the immediate vicinity of the aperture, the size of the resulting area of illumination is significantly reduced. If the illuminated surface (top) is left as a continuous conductor with an array of circular holes in it and the bottom is segmented as described above, a photonic funnel can be created. To minimize the effective broadening of the holes due to surface plasmons on the bottom plane, it may be desirable to create a very sharp edge at this point in either a conducting wall or in an insulator with less available charge to minimize any surface-plasmons/photon interaction. It is important to note that the insulator (in the case of a semiconductor) should have a band gap significantly larger than the frequency of the photons, which will be propagating through it.

Figure 4:
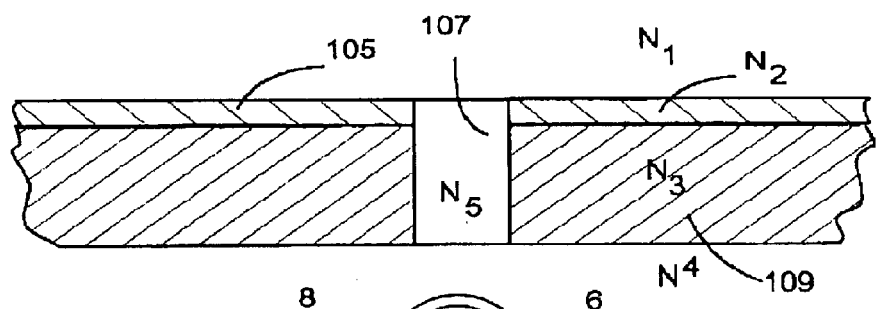
FIG. 4 is a cross-sectional view of a thin metallic film that covers a non-metallic substrate material with an aperture through both the metal film and substrate having a diameter less than the wavelength of the incident light.

A first improved geometry for the hole array that produces a smaller illumination pattern is shown in FIG. 4 of the drawings. A thin metal conductive film 105 exhibiting the index $N_2$ is affixed to a substrate 109 constructed of a dielectric material having the index $N_3$ and a bandgap that is larger than the frequency of the illumination of light. In fluorescence studies, if multi-photon excitement is employed, the bandgap should be larger than the sum of the photonic energies of the photons that would be simultaneously absorbed by the fluorophore. The thin layer of conducting material 105 should be thicker than the skin depth of the metal at the chosen wavelengths. The geometry and composition of the heterogeneous structure seen in FIG. 4 should be chosen so that a maximum of transmission of illumination occurs through the hole 107 at the chosen illumination wavelength. A tunable or broad band light source may also be used to trune the wavelength to predetermined hole dimensions.

Figure 5:
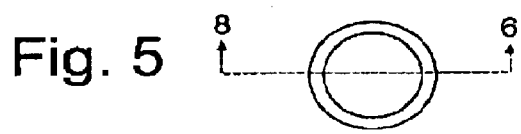
FIG. 5 is a view illustrating the approximate size of the circular area illuminated by the light transmitted through the aperture in structure shown in FIG. 4.
Figure 6:
FIG. 6 is a graph illustrating the illumination intensity in the illuminated area taken along the line 6—6 of FIG. 5.

The advantage of the geometry shown in FIG. 4 over that presented in FIG. 1 results from the fact that there is no coupling of plasmons from the upper surface of the film 106 to the lower surface of the dielectric material 109. This reduced coupling creates a smaller and more defined illumination pattern with steeper side slopes as illustrated in FIGS. 5 and 6. It is unclear, though, what happens to the energy at the corner interface of the hole 107, the metal film 105 and the dielectric substrate 109, that is, at the boundary of the materials having the indices $N_5$, $N_2$ and $N_3$. If $N_1$, $N_4$ and $N_5$ are not all substantially equal to one (1.0), combinations of differing indices could be used to tailor the transmission of the array apertures for a specific wavelength or method of illuminating the structure. For example, $N_1$ could be the index associated with an optical fiber, which would be coupled to a remote light source.

Figure 3:
FIG. 3 is a graph illustrating the illumination intensity in the illuminated area taken along the line 3—3 of FIG. 2.
Figure 7:
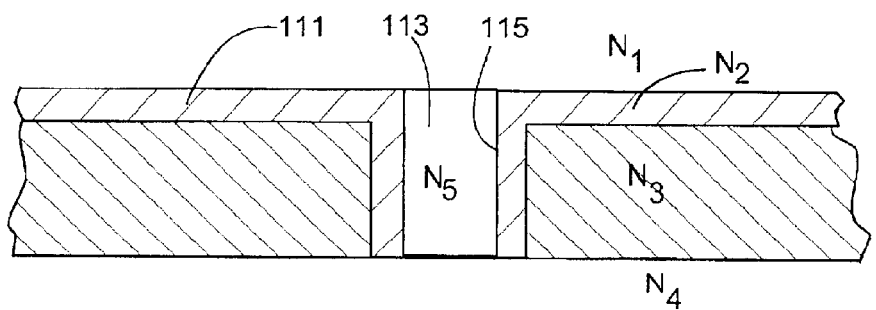
FIG. 7 is a cross-sectional view of a thin metallic film that covers the surface of a non-metallic substrate material as well as the sidewalls of an aperture through the substrate with the aperture having a diameter less than the wavelength of the incident light.
Figure 8:
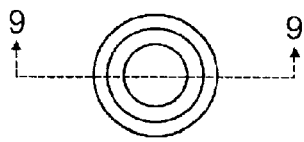
FIG. 8 is a view illustrating the approximate size of the circular area illuminated by the light transmitted through the aperture in the structure shown in FIG. 7.
Figure 9:
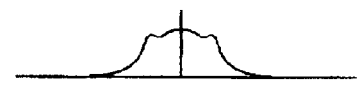
FIG. 9 is a graph illustrating the illumination intensity in the illuminated area taken along the line 9—9 of FIG. 8.

A second hole array structure for reducing the size and increasing the density of the spot illumination is shown in FIG. 7. As before, the structure of FIG. 7 presents at its upper surface a continuous conducting thin film metallic film 111 having the index $N_2$. The structure differs from that shown in FIG. 4 in that the metallic coating is continued into the interior of the hole 113 as seen at 115. If the thickness of metal layer 115 in the hole interior were greater than skin depth, the effects seen in optically thick metal films as shown in FIG. 1 would be duplicated from the standpoint of optical transmission through the holes. However, a smaller and more concentrated output light pattern is achieved by limiting the propagation length of SPs at the exit surface to the thickness of the film in the hole. Limiting the size of the excited surface area surrounding the hole exit produces a concentrated, circular light pattern as seen in FIG. 8 rather than prolate pattern seen in FIG. 3, thus limiting the size of the light source in only one of its two dimensions. As is the case with the structure shown in FIG. 4, the indices $N_1$, $N_4$ and $N_5$ may be equivalent to 1 in the simplest configuration but other combinations be used to tune the holes for a specific resonance. FIG. 9 graphs the steeply skirted intensity distribution expected across the circular light pattern along the line 9—9 of FIG. 8.

Figure 10:
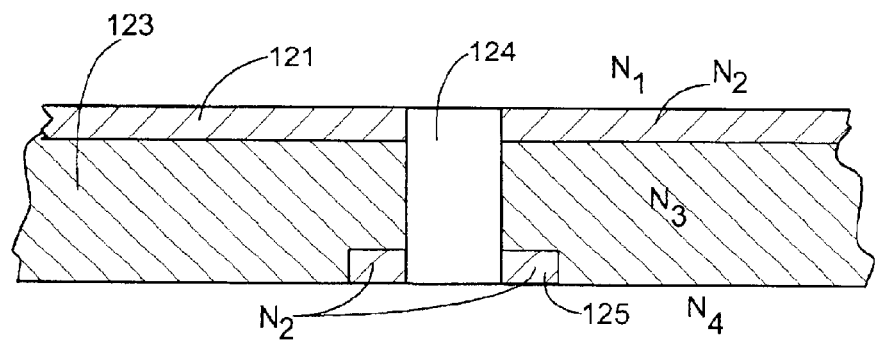
FIG. 10 is a cross-sectional view of a thin metallic film which covers a non-metallic substrate material, an aperture through the substrate, and a thin, annular metallic ring surrounding the aperture on the opposing surface of the substrate, with the aperture having a diameter less than the wavelength of the incident light.
Figure 11:
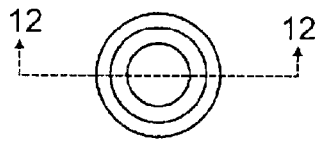
FIG. 11 is a view illustrating the approximate size of the circular area illuminated by the light transmitted through the aperture in the structure shown in FIG. 10.
Figure 12:
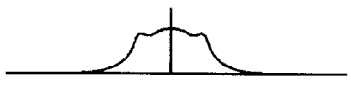
FIG. 12 is a graph illustrating the illumination intensity in the illuminated area taken along the line 11—11 of FIG. 10.

A third structure that may be used as a source of concentrated light is shown in FIG. 10. As in the structures shown in FIGS. 4 and 7, a thin metallic film 121 covers the upper surface of a dielectric substrate 123. A hole 124 through the film 121 and the substrate 123 is not lined with a conductor as in FIG. 7. Instead, an annular ring 125 of conductive material surrounds the exit end of hole 124 at the lower surface of the substrate 123. The conductive ring 125 increases the coupling with the film 124 to improve light transmission through the hole 124 but does not permit the surface excitations surrounding the hole exit to spread beyond the outer periphery of the ring 125, thereby again achieving the more concentrated, steep skirted output light pattern shown in FIGS. 11 and 12.

Figure 13:
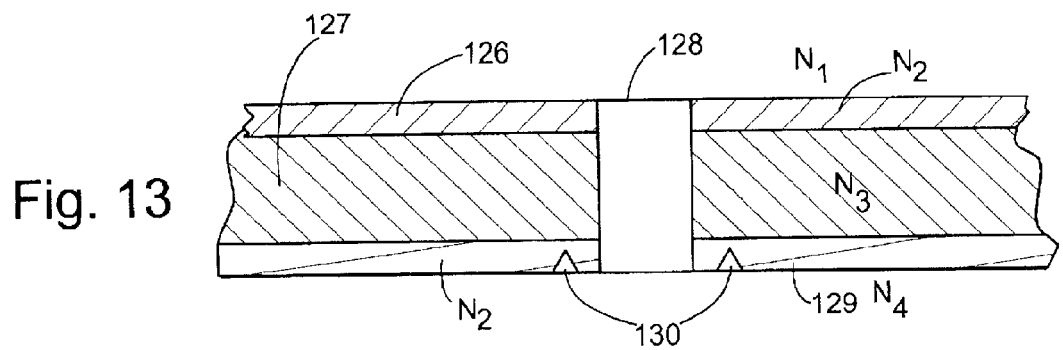
FIG. 13 is a cross-sectional view of a hole structure in which a thin metallic film which covers both surfaces of a non-metallic substrate material, and an annular notch is cut into the film at the exit surface which surrounds and is spaced from the hole.
Figure 14:
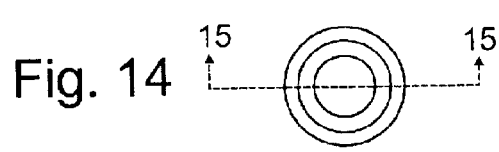
FIG. 14 is a view illustrating the approximate size of the circular area illuminated by the light transmitted through the aperture in the structure shown in FIG. 13.
Figure 15:
FIG. 15 is a graph illustrating the illumination intensity in the illuminated area taken along the line 15—15 of FIG. 14.

FIG. 13 shows still another structure in which a dielectric substrate 127 is coated on its upper surface with a metallic film 126 and on its lower surface with a metallic film 129. The hole 128 passes through both films and through the substrate and its side walls are not coated. An annular groove seen at 130 is formed in the film 129 and surrounds and is spaced from the hole 128. The groove has a nominal outside diameter of 25 nm and inside diameter of 20 nm. The depth of the groove must be at least the skin depth of the material, thereby acting as insulator with respect to induced surface excitations. The groove may have any convenient shape and may be rectangular or triangular as well as circular. Note that, by using a groove of the type shown in FIG. 13, a 200 nm thick metallic structure may be used instead of a dielectric substrate, so that the hole is effectively lined by a conductor. In both cases, the groove serves to contain the coupled electron excitation within a surface area close to the hole exit, thereby preventing unwanted spreading of the illumination pattern. The illumination pattern produced by the hole and groove configuration of FIG. 13 is depicted in FIGS. 14 and 15.

Figure 16:
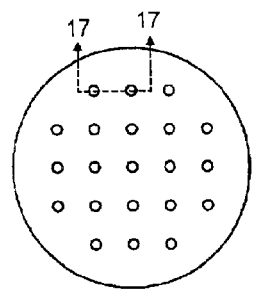
FIG. 16 is an end plan view of a multi-aperture probe constructed in accordance with the invention.
Figure 17:
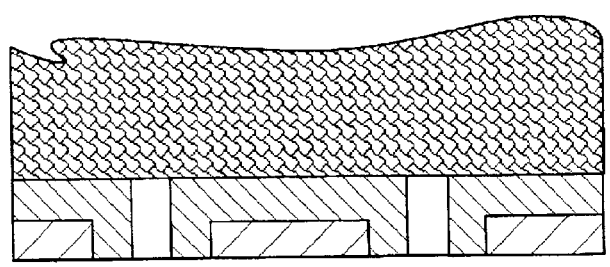
FIG. 17 is a cross sectional view of the probe seen in FIG. 16 take along the line 17—17.
Figure 18:
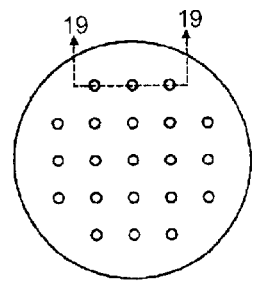
FIG. 18 is an end plan view of an alternative structure for the multi-aperture probe constructed in accordance with the invention.
Figure 19:
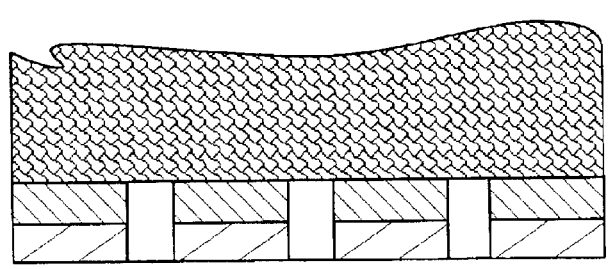
FIG. 19 is a cross sectional view of the probe seen in FIG. 18 taken along the line 19—19.

As will be discussed later in conjunction with FIG. 22, the principles of the invention may be used to construct a multi-aperture probe (MAP) which may be used to advantage in scanning microscope. FIGS. 16 and 17 illustrate a MAP structure using holes with electrically conducting sidewalls of the type discussed earlier in connection with FIGS. 7 and 13, while FIGS. 18 and 19 show the construction of a MAP having holes whose sidewalls are in part non-conducting as previously discussed in connection with FIGS. 4 and 10 of the drawings.

As also discussed above, another approach to eliminating the prolate pattern is to align the polarization with a slit. If the material through which the photons are propagating has low charge availability (as in slit), there can be very few or no surface plasmons. Also, the propagation of light is supported along the slit and throughput should be higher for an array of slits versus an array of circular holes of the same area. Work done on slits much smaller than the transmitted wavelength (32 nm slit) [see Astilean, Lalanne and Palamaru "Light transmission through metallic channels much smaller than the wavelength" *Optics Communications* 175 265–273 March 2000] in optically thick metal films shows peaks in the NIR and visible transmission versus incident wavelength curves with maxima in the order of 80% efficiency for the plate with a grid spacing of 900 nm. For the strongest peak, 1.183 $\mu$m, this is an extraordinary amount in that almost 10 times the amount of light impinging on the slits is transmitted through them. Also reported are slits of 10 nm widths, which when excited at resonance, achieve 10% efficiency. Astilean et al. conclude that the resonance condition is not only a function of the SP resonance but that the metallic wall linings of the slits act as Fabry-Pérot cavities and that greatly enhanced transmissions occur when the slit satisfies the Fabry-Pérot resonance condition [see Born, M. and Wolf, E. *Principles of Optics.* Cambridge University Press 6$^{th}$ ed. 1980 p.326 ] with an effective index of refraction which depends strongly on the slit width and material.

Figure 20:
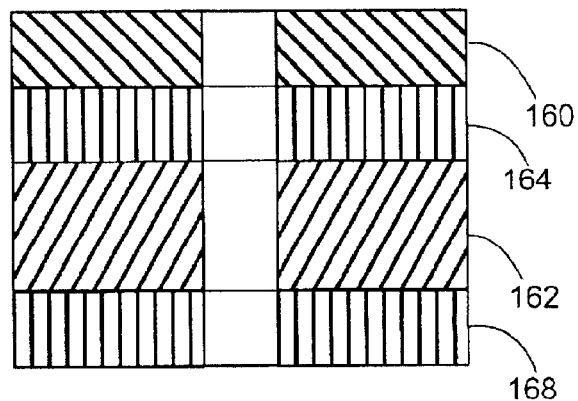
FIG. 20 is a cross sectional view of an alternative light barrier structure employing "good" and "bad" metal layers.

FIG. 20 shows still another configuration which utilizes the principles of the present invention. In this arrangement, the light barrier is composed of three different materials: a "good" metal layer 160 over a substrate consisting of an insulator 162 sandwiched between two layers of "bad metal" 164 and 168. As with the other structures, the "good" metal used in layer 160 is one in which the surface plasmons will decay over a relatively long distance as determined by the surface roughness of the film 160 (which includes the holes) and the relative values of the real and imaginary parts of the dielectric function of film 160 (where a small imaginary part provides a long delay decay length). In contrast, the "bad" metal used in the layers 164 and 168 has a dielectric function with a large imaginary part so that the surface plasmons decay more quickly over a relatively short decay length.

The "bad" metal used in layers 164 and 168 preferably exhibits two additional properties which make a significant contribution to the creation of nanometric light sources. First, the "bad metal" should be opaque to the light emitted from the surface of the "good" metal in thin films. Second, the resonance of the "bad" metal layer(s) should be should be very different than that of the "good" metal. The resonance of the metal layers is determined only by the real part of the dielectric function for metal, the surface roughness of the metal layers, and the dielectric functions of the materials on either side of the metal layer.

The insulator 162 ensures that there can be no surface plasmon communication from top to bottom through bulk plasmons or any other direct electronic interaction. Note, however, that the presence of the insulator 162 may not required if the bad metal satisfies the criteria expressed above; that is, is opaque to light emitted from the good metal layer and has a resonance that is very different from the good metal layer.

For the all of the structures described in connection with FIGS. 4–20, the thickness of the substrate supporting the good metal layer should be on the order of 200 nm. The diameter of the hole should be between about 10 nm and 50 nm. The metallic film layers should, as noted earlier, be at least skin depth of the electronic excitation and may be formed, for example, from gold, silver, aluminum, beryllium, rhenium, osmium, potassium, rubidium, cesium, rhenium oxide, tungsten oxide, copper or titanium. Suitable dielectric and "bad metal" substrate materials include germanium, silicon dioxide, silicon nitride, alumina, chromia, some forms of carbon and many other materials. The aperture array with sub-wavelength holes may be fabricated using available focused ion beam (FIB) milling techniques.

The physical structures for producing very small spot and slit illumination may be used to advantage in a number of different applications as next described.

Optical Data Storage using Small Spot Illumination

Figure 21:
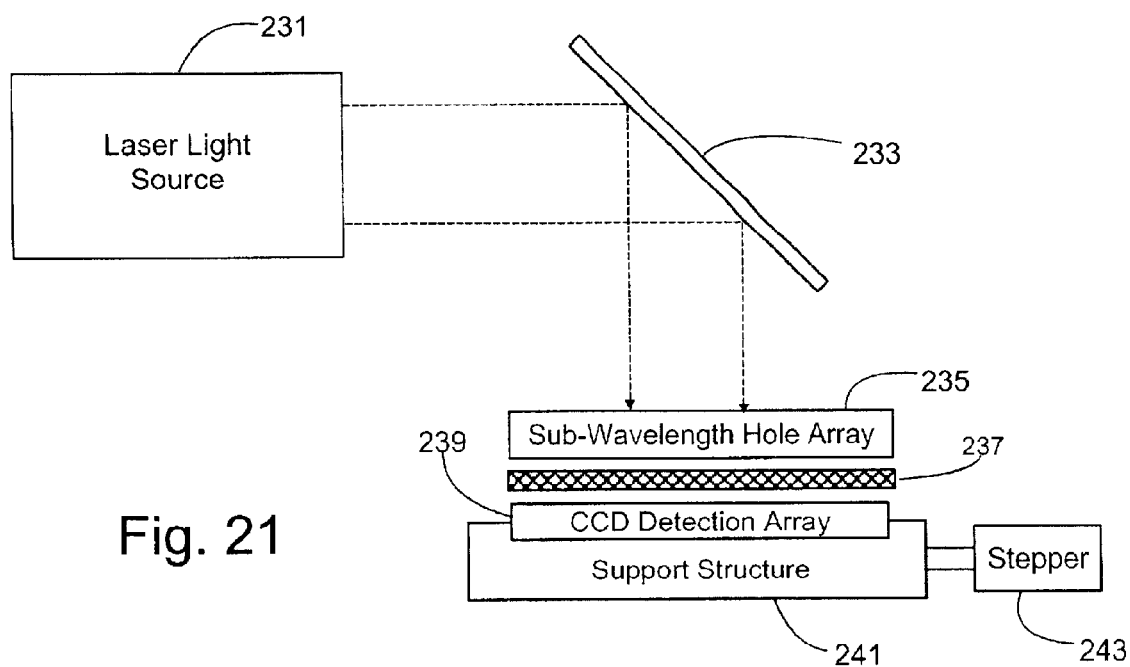
FIG. 21 is a schematic diagram of a data storage device that uses an array of nanometric holes to illuminate a data storage array as contemplated by the invention.

FIG. 21 illustrates the manner in which a nanometric light source array of the type contemplated by the invention may be used to increase the storage density in an optical storage device. The optical memory consists of a light source 231, such a solid state NIR laser as shown in FIG. 21. The light from the source 231 is directed onto the metallic film surface of a nanometric hole array 235 using a fold mirror 233. The nanometric hole array 235 collects and funnels the light such that an array of discrete areas of illumination are directed toward the optical storage medium 237. At each area of illumination, a data value stored at that location in the storage medium controls the intensity of the light which passes to a pixel location on a charge coupled diode array (CCD) 239 and hence controls the output data value from that CCD pixel. The holes in the array 239, the data storage regions in the medium 237, and the pixel locations in the CCD 239 are equally spaced so that they are properly aligned. A translation mechanism effects movement of the storage medium relative to the hole array in incremental steps, with each step distance being equal to the aperture size.

Currently, commercially available CCD arrays have pixel sizes no smaller than $(4 \mu m)^2$. If this is a limiting case, optics between the storage medium and the CCD array could be used to allow less movement. The step size would then be down to that demanded by the Rayleigh criterion.

Note also that the amount of data stored at each pixel location may be increased by storing more than two signal levels; for example, gray scale or color values may be stored as analog signal magnitudes at each storage location.

Surface Plasmon Enhanced Microscopy

Figure 22:
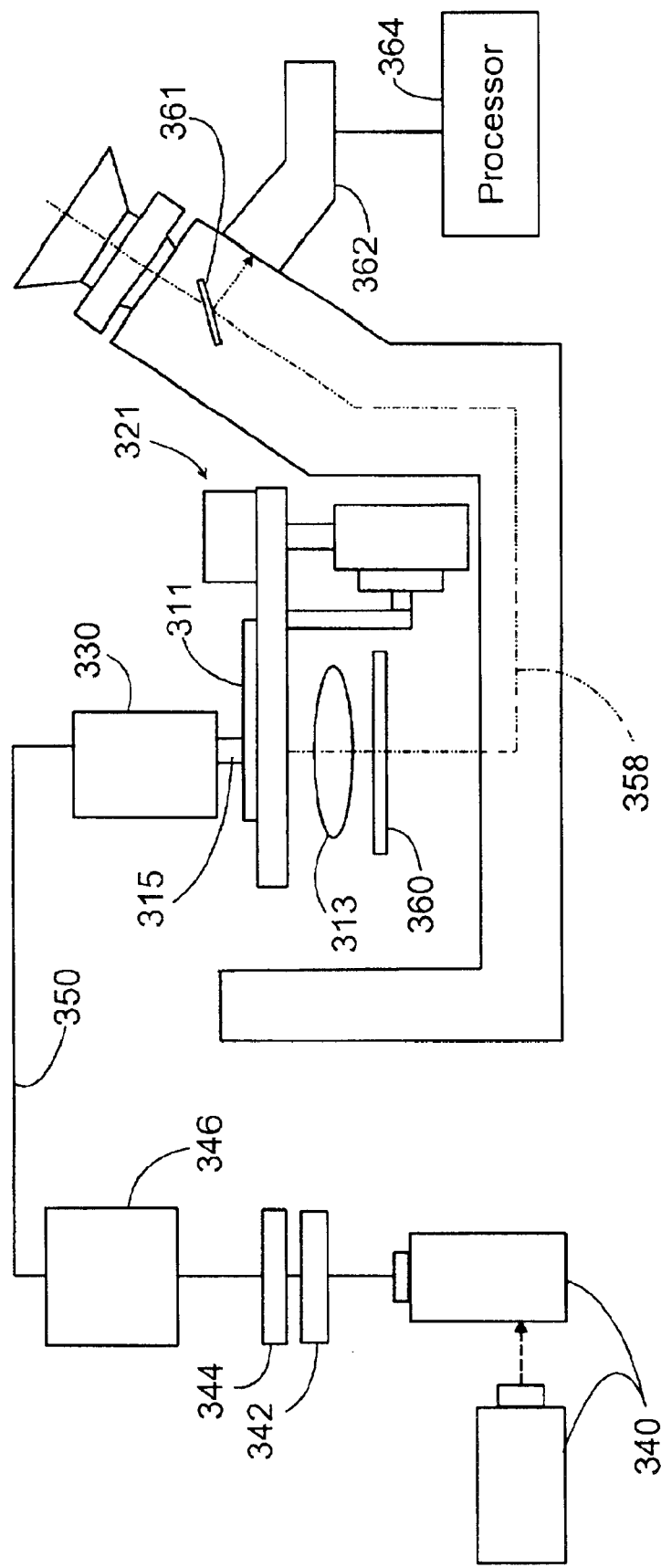
FIG. 22 is a schematic diagram of a Surface Plasmon Enhanced Microscope (SPEM) which embodies the invention.

FIG. 22 of the drawings illustrates the use of the nanosecond light source array as contemplated by the invention to construct a "Surface Plasmon Enhanced Microscopy" SPEM). A sample 311 is placed between the objective lens 313 of the microscope and the multi-aperture probe (MAP) 315. The sample is mounted on a transparent, flat substrate placed on a translation stage 321 capable of nanometric movement. The MAP 315 is then moved into close proximity to the sample 311 and held in place by a compressive force module or proximity sensor 330. In fluorescence mode, light is emitted by a light source, such as a pumped laser, a light emitting diode, an arc lamp or other white light generator, 340 and transmitted via neutral density filters 342, polarizers 344, a fiber coupler 346 and an optical fiber 350 down to its terminus at the MAP 315, where it is emitted through an array of holes in a mask that has been fabricated onto the end of the optical fiber. The light leaving the holes strikes the sample 311 at its surface. The far field light path 358 from the objective 313 passes through a low pass filter 360 to a beam splitter or mirrored shutter at 361 which redirects the light to a cooled charge coupled detector (CCD) 362 that converts the light into electrical signals which are passed to the processor 364 which performs image capture (frame grabbing) and other image processing functions.

In fluorescence mode, the impinging light is absorbed by fluorophores, which resonate, emitting photons at a different frequency. The fluorescent light is collected in the far field by the objective lens and then transmitted into oculars 370 or to the data collection device (e.g., the CCD array 362.)

Once the entire sample has been illuminated by the array of apertures, the resulting fluorescence is collected in the far-field. The MAP 315 is then raised and the sample 311 is indexed to the next position and another set of measurements is made. This process is repeated until the space between the spots, 250 nm to 600 nm, has been scanned. This is a much easier and faster task than with NSOM.

It should be clear from the above discussion that it would be difficult to design a probe of the types above with the aim of efficiently transmitting a multiple of wavelengths chosen to maximize the excitation of a suite of fluorophores. One solution is to make tunable MAPs by dynamically modifying the effective dielectric function of the secondary metal (the metal probably would be replaced by a semiconductor) during operation. By changing the dielectric function of the surface below the primary metal, the frequency of emission can be changed substantially. [See Kim, T. J., Thio, T., Ebbesen, T. W., Grupp, D. E. & Lezec, H. J. Control of optical transmission through metals perforated with sub-wavelength hole arrays." *Opt. Lett.* 24, 256–258 (1999) using a twisted-nematic liquid crystal under an array]. It has also been shown that the application of a magnetic field has strong effects on the dielectric function [see Strelniker, Y. M. & Bergman, D. "Optical transmission through metal films with a subwavelength hole array in the presence of a magnetic field." *Phys. Rev. B* 59, 12763–12766 (1999). Another method of tuning the array may be to have domains surrounding the apertures in which the density of electrons can be modified by passing an electric current through that domain. The small capacitance of the domain would affect the density of the electrons and, hence, the resonance of the surface plasmons.

Multiple MAPs could be constructed with parameters tailored to each fluorophore of the chosen suite. Each probe would be interfaced to the sample and would present a roughly monochromatic source. As the widths of the peaks of the resonances of the MAPs will be broad (about 20 nm FWHM), the fluorophores will have to be chosen well with significant distances between their excitement wavelengths. In this case, the SPEM will probably be limited to only a few (maybe 6 or so) different fluorophores. However, the quantum dot offers great promise. Bruchez et al. ["Semiconductor Nanocrystals as Fluorescent Biological Labels" *Science* 281 1998.] have successfully used quantum dots as biological markers. Importantly, the quantum dots may be excited by a single source and to be multiplexed such that multitudes of dots can be detected and identified simultaneously.

SPEM has been conceived with clinical and basic research applications in mind and the user interactions have been structured to make it an easy technique to use. The basic steps, for both clinical and basic research use, are:

1. Prepare the sample
2. Select the cells of interest from the slide
3. SPEM automatically captures the data
4. Review the results and generate specific database analyses.

Step 1. Prepare the Sample: In the clinical application the only additional sample preparation step required is to add the antibody-label reagent to the slide and incubate. The tissue sample preparation steps currently in use for pathology slides are done prior to adding the SPEM labeling reagents (antibody-fluor complexes). Generally for cell culture samples the cells will be embedded in paraffin and then treated as tissue samples for the purposes of preparing them for analysis in SPEM. It would be possible, though, by using an actively cooled, transparent, thermally conductive substrate, to investigate frozen tissue samples.

Step 2. Select the cells of interest from the slide: With SPEM the user looks at the slides with a standard far-field microscope prior to the high resolution investigation. This allows the user to make use of the morphology data available today and select cells for further analysis that are the most interesting. To accomplish this, the SPEM system will incorporate a module that allows the user to digitally mark (record the x-y coordinates) the cells for further analysis. This allows the user to gather data on different cell types, cells at different stages of the cell cycle, and multiple cells of the same type to increase the statistical power of the near-field analysis. This also should allow the user to create multiple slides from the same cell representing sequential cuts from the microtome. The resulting SPEM data can then be reconstructed to create a three dimensional data set of protein locations and expression.

Step 3. SPEM automatically captures the data: The SPEM system will execute the illumination and far-field collection steps described above to generate a database of protein localization and expression information.

Step 4. Review the results and generate specific database analyses: The database created in the previous step provides the user with the ability to create custom queries to address the biological or clinical question under investigation. It is expected that as SPEM matures there would be a library of specific database queries that would be used. In particular, for clinical use pathologists would have a set of standard analyses that are performed with the SPEM to elucidate molecular signatures of cancer.

SPEM generates a data file consisting of the location of every fluor detected in the cell, and the protein with which it is associated. This data file can be analyzed in a number of ways, including:

i) Generating a map of each protein's location within the cell that is superimposed on an image of the cell.
ii) Providing the number of copies of each protein that were detected.
iii) Statistics for a number of conditions:
   (a) Percentage of copies in the nucleus or cytoplasm
   (b) Number of copies of a protein that are within a user specified distance of either another protein, or a cellular feature (e.g. cell membrane)
   (c) Comparisons between cells (e.g. mutant and wild type)
   (d) Comparisons of protein locations and expression levels between cells at different stages of the cell cycle.
   (e) Comparisons between cells at different developmental levels
iv) Assist in the selection of therapies and determination of prognoses for cancer patients based on molecular signatures of cancers.

The strengths of SPEM include:
(1) The ability to obtain protein localization and expression data for multiple proteins in a cell from either cell culture or a tissue sample.

(2) Localization resolution better than 75 nm, and possibly as low as 10 nm.

(3) Protein expression data based on protein levels, not on mRNA.

(4) Permits the study of low copy number proteins.

(5) Less sensitive to vibrations than NSOM and Atomic Force Microscopy. The level of vibration isolation that is needed is similar to standard microscopy techniques.

The MAP used in a SPEM should:

(1) Have an array 75 nm (or smaller) holes that can illuminate a tissue sample with enough energy to excite fluors that have been bound to specific proteins in the sample.

(2) Have a diameter of at least 20 $\mu$m in order to cover a typical cell.

(3) Have the holes in the array spaced far enough apart to permit collection of optical data from the fluors using far-field optics (greater than the distance imposed by the Rayleigh criterion for the objective lens being used for collection and the emission wavelength of the lowest frequency fluorophore.)

(4) Maintain high resolution registration of the locations of the holes in the array relative to the far-field optics.

(5) Have optical and thermal conductances that are high enough to avoid deteriorating levels of thermal expansion of the MAP and heating of the sample.

Fabrication of the MAP should be undertaken with the following parameters in mind: the ability to control aperture size (geometry and thickness); the ability to control aperture spacing; the nature of the materials (e.g. purity, continuity); and the characteristics of the coating needed (e.g. continuity and thickness).

In the metal film experiments above, the holes in the films were created by two methods, both achieving excellent cylindrical geometry. In the Sönnichsen experiments, a suspension of polystyrene beads was spin-cast onto a very thin (1 nm) adhesive layer on a glass substrate and a subsequent metal film evaporated onto the adhesive and the spheres. The spheres and the metal covering them were then removed by ultrasonification. In the experiments conducted by NEC Research, the holes were created by focused ion beam milling (FIB). This method allowed more latitude in the hole size and spacing in the metal film.

Because the preferred structures are both heterogeneous and require that the hole spacing is uniform (for scanning purposes) or at least well characterized and repeatable from MAP to MAP, the method of spin casting is not useful. FIB can be used but may be expensive for the use of SPEM in clinical settings. Another proposed method of fabrication is to use a naturally occurring structure of alumina. Alumina can be anodically etched to produce a uniform nanometric, closely packed honeycomb structure over large areas [see Keller et al. *J. Electrochem. Soc.* 100 411 1953, Thompson et al. *Nature* 272 433 1978] By using micromanipulation, holes could be filled with an insulator or conductor leaving only apertures where desired. The structure would then be plated with the chosen electrical conductor and the bottom surface milled away using FIB.

The SPEM microscope illustrated in FIG. 22 may be implemented using commercially available components. An inverted fluorescence microscope such as a Zeiss IM35 or a model from the Zeiss Axiovert family would be suitable for modification. The microscope should have at minimum, two high numerical aperture (1.3 or greater) Plan-Apochromat objectives; one for high magnification (100 ×) and one for medium magnification (63×.) Because the exciting photons are traveling in the MAP, and there is no ultraviolet light involved, special glasses and coatings are not required. The above objectives have been corrected at the red, green and blue wavelengths for chromatic aberration and will, hence, not be a problem with different fluorescing colors.

At low levels of fluorescence (low light input is desired to minimize the effects of photobleaching and possibly, with two-photon excitation, stimulated emission depletion) that may be seen in the SPEM, cooling is required when using a charge coupled device (CCD) array to maximize signal to noise ratio. Zeiss manufactures a suitable high resolution (1300×1030 pixels) thermoelectrically cooled CCD array/frame grabber package called Axiocam with color density of 14 bit color classification which is adequate for purposes of multiple fluorescence capture and discrimination. The Axiocam is sold by the Microscope Division of Carl Zeiss with software called AxioVision and, since the CCD array, thermoelectric cooler, frame grabber and image analysis software come integrated and designed specifically to mate to the Axio microscopes.

Translation of the sample relative to the MAP and collection optics requires a 3axis translation stage shown generally at 321 in FIG. 22. The step size of the translation stage and its resolution should be less than the required resolution desired of the spatial resolution of fluorophores in the sample. Mad City Labs (Madison, Wis.) offers such a device called the Nanobio350/ The controller is delivered with LabView software to make integration with the imaging system easier.

Although the above-noted CCD array is color sensitive and discriminating, it is sensitive into the wavelength regime (NIR) of the emission laser. So that the pixels are not saturated with the stimulating radiation and to avoid more computation than necessary, an optical low pass filter should be placed in the path between the CCD input and the objective lens of the microscope. There are numerous suppliers for such filters. If a laser light source is used, a grating compensation system may need to be employed to avoid the dispersion that would otherwise occur in the fiber. These are available from Coherent.

The current factor that limits the number of proteins that can be simultaneously characterized using SPEM is the limited availability of spectrally distinguishable fluorophores. Many researchers are working on this issue and it is expected that SPEM will benefit greatly from these efforts. Some of the more interesting candidates are described below.

Because the MAP will be designed for efficient transmission of one specific wavelength of light, a set of fluorophores that can all be excited by the same wavelength will need to be selected. There are two promising methods for this: 1) two-photon excitation of fluorescent dyes, using an infrared light source, and 2) quantum dots, using a blue-violet light source. For fluorescent dyes, we would need a set with well-separated emission wavelengths and narrow spectral peaks. At least two vendors offer products that meet these criteria: Molecular Probes of Eugene, Oreg. offers a set of seven BODIPY dyes, and Amersham Pharmacia Biotech (www.apbiotech.com) offers a set of five Cy dyes. In addition, new dyes are introduced frequently. Quantum dots are not yet commercially available for biochemical labeling, but are expected to be in the near future. By tailoring the size of the cavity, quantum dots can be made with any desired emission wavelength, so conceivably more than seven could be used within the visible-light spectrum. However, quantum dots are significantly larger than fluorescent dye molecules, 10–20 nm vs. 1–1.4 nm effective diameter. This makes fluorescent dyes the more attractive option. However, if two-photon excitation overheats the SPEM probe, quantum dots will be used for the multiple-labeling experiments.

Quantum dots are nanometer size semiconductor particles with sub-wavelength size pits grown or machined into them. The dimension of the pit determines the color of light emitted from a quantum dot. The pits have dimensions 2 nm (for green light) to 5 nm (for red light), and the overall particle has a dimension of 10–20 nm. It should be easier to develop new quantum dots with precisely tuned emission wavelengths (compared to developing a new fluorophore) by tailoring the exact dimensions of the pits in the quantum dots. Quantum dots have a narrow spectral peak width, with a fall width at half maximum (FWHM) of 30–35 nm [see M. Bruchez Jr., M. Moronne, P. Gin, S. Weiss, and A. P. Alivisatos, "Semiconductor nanocrystals as Fluorescent Biological Labels", *Science*, 281, Sep. 25, 1998, p. 2013–2016.]. This is comparable to the seven Molecular Probes BODIDY fluorescent dyes, which have spectral peak widths of 22–35 nm FWHM [Figure 1.2 of Molecular Probes CD handbook]. Narrow spectral peak widths allow many colors to be distinguished, allowing many reporters to be used simultaneously.

In addition to fluorescent dyes, and quantum dots mentioned above, other types of reporters are also in development. Multiplexing arrangements, which allow a more complex code in each reporter tag, are also in development.

At present, all of these approaches produce tags that are too large. Nanobarcodes (10–20 nm diameter×30 nm long) consist of chips with stripes of reflective gold, silver, and platinum metal. The width and spacing of the lines can be altered. Colloidal particles have been used to tag beads for combinatorial synthesis [see Battersby B J, Bryant D, Meutermans W, Matthews D, Smythe M L, Trau M, Toward Larger Chemical Libraries: "Encoding with Fluorescent Colloids in Combinatorial Chemistry", *Journal of the American Chemical Society*, 122: (9) 2138–2139, Mar. 8 2000]. In this scheme, a 100-micron diameter bead holds multiple 1-micron diameter colloidal particles. Each type of colloidal particle holds a unique combination of fluorescent dyes. PEBBLE (Probe Encapsulated By Biologically Localized Embedding) sensors consist of fluorescent dyes encapsulated in a polymer matrix; these particles can be as small as 20 nm. While these have been used for sensing ion concentrations in cells [see 1 Clark, Heather A; Hoyer, Marion; Philbert, Martin A; Kopelman, Raoul, "Optical Nanosensors for Chemical Analysis inside Single Living Cells. 1. Fabrication, Characterization, and Methods for Intracellular Delivery of PEBBLE Sensors", *Analytical Chemistry*, 1999, v.71, n.21, pp.4831–4836; and Clark, Heather A; Kopelman, Raoul; Tjalkens, Ron; Philbert, Martin A, "Optical Nanosensors for Chemical Analysis inside Single living Cells. 2. Sensors for pH and Calcium and the Intracellular Application of PEBBLE Sensors", *Analytical Chemistry*, 1999, v.71, n.21, pp.4837–4843], the technique may be extendable to labeling proteins.

It is possible that the light output from the holes in the MAP will cause illumination of fluorophores or quantum dots in planes substantially below the surface over which the MAP sits. These molecules could be excited by the spreading photons and may, therefore, not be directly in line with the axis of the holes but could be in between the axes of several holes resulting in a weak magnitude positive signal at more than one location, yielding incorrect spatial information and possibly concentration or color. Methods to reduce this misinformation could be (but certainly aren't limited) to making the tissue sample or the image sample as thin as possible or using multi photon excitement. Because of the squared dependence of the two photon excitement of location, there will be a substantially higher chance of two photons arriving concurrently directly in line with the axes of the holes than anywhere else below the MAP, potentially enhancing resolution.

Other modifications to the MAP may be implemented to modify the resonant wavelengths. One method would be to change the in-plane magnetic field of the MAP. It has been shown the direction and the magnitude of the field can dramatically affect the resonant wavelengths by affecting the effective dielectric functions of the metals. Another method may be to change the density of electrons in the metals to also affect the effective dielectric functions. This could be achieved in numerous fashions. The simplest would be simply to "pump" electrons into the metal. Possibly, localization of charges and/or magnetic fields could allow the MAP to perform read and write operations in storage media and could be used a polychromatic excitation source for fluorophores.

High Resolution, High Throughput Photolithography

The ability to create spots of light with diameters that are well below the wavelength of the light forms the basis of a new approach to lithography. The array structures described above can be modified in a very simple way to achieve a useful tool for lithography. In the structures discussed in connection with FIGS. 4–20 above, all of the apertures in the array penetrate the SPEI light barrier and as a result all emit light. For lithography, all but the central aperture in a set (the smallest number of apertures required to establish the resonant condition) would be changed from apertures that go through the barrier to elements of surface roughness (dimples) that are deeper than the skin depth and the same diameter as the aperture. Alternatively, the dimples surrounding the central aperture can be replaced with an annular groove having a width equal to the emitting hole diameter and a depth greater than skin depth. This technique allows the extraordinary transmission to be retained while only providing emission from the central aperture. This central aperture then becomes the scanned element that is used to write to the photoresist to perform lithography.

Figure 23:
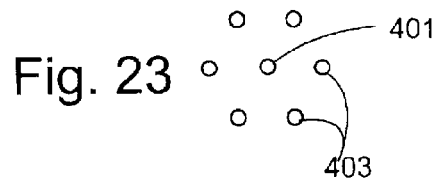
Figure 24:

This structure is shown schematically in FIGS. 23 and 24. FIG. 23 illustrates a hexagonal pattern of apertures (one emitting aperture 401 surrounded by six dimples 403) where the relationship between the resonant wavelength and the spacing is governed by the following equation[17]

$$\lambda_{max} = a_0 (i^2 + j^2)^{-1/2} \left( \frac{\varepsilon_1 \varepsilon_2}{\varepsilon_1 + \varepsilon_2} \right)^{1/2}$$

where: $\lambda$ is the wavelength, $\epsilon_1$ and $\epsilon_2$ are the real portions of the dielectric constants for the metal and the surrounding medium, $a_0$ is the lattice constant (spacing between dimples/apertures), while i and j are integers characterizing the particular branch of the surface plasmon dispersion.

FIG. 24 shows an alternative arrangement in which the single emitting aperture 407 is surrounded by an annular groove 409 with a width equal to the diameter of the emitting hole. In accordance with the invention, means are employed for limiting the extent of surface plasmon excitation at the exit surface of the emitting hole to the hole itself, or to a small area surrounding the rim of the hole at its exit, thereby confining the area of illumination to achieve higher resolution. All of the light barrier configurations described above in connection with FIGS. 4–20 may be employed to limit the illumination area produced by the emitting hole.

The optical system required to execute SPEI lithography is very simple; there are no reduction lenses or steering mirrors,. All that is required is a somewhat mono-chromatic light source, such as a filtered broadband (e.g. Hg lamp) source or a laser, the SPEI device, a subnanometer translation stage (e.g. piezo system from Mad City Labs), a proximity sensor to maintain the SPEI device at a proper photoresist distance, and a photoresist coated wafer.

Three techniques may be used to improve the throughput of a lithographic process. First, surface plasmon resonance is used to achieve high light transmission in order to increase the speed at which the photoresist can be patterned. The other two approaches increase the parallelism of the writing operation as described below.

The first level of parallelism is achieved by the creation of a SPEM array that contains one emitting aperture for each IC on a wafer. The spacing between emitting apertures will be the same as the spacing between ICs on the wafer. By doing this, the same pattern can be written to all ICs at the same time. To achieve a level of stiffness that maintains the flatness of the device and therefore achieves a uniform device-to-photoresist spacing, a transmissive substrate may be prepared using the same techniques used to prepare semiconductor wafers and fabricate the SPEI device on the wafer. The SPEI device should match the index of refraction of the glass instead of air. The resulting wafer/SPEI device should be rigid enough to allow for a constant CD to be maintained; otherwise, the SPEI device would have to be farther from the photoresist and divergence of the emitted light will increase the minimum CD that can be achieved. If the device is not rigid enough we expect to fabricate structural elements into it to achieve the desired stiffness. The light source should provide uniform illumination over the wafer diameter.

The second level of parallelism is achieved by writing multiple features within an IC in parallel. This is achieved with two modifications to the system. First, "shutters" are added between the light source and the SPEI device. Second, an SPEI device is constructed that has provides a palette of different shapes. The two basic shapes that would be included are a circular (or square) aperture and a line segment. Each of these shapes is preferably provided in different sizes (diameters for the circular apertures, and lengths and widths for the line segments), and the line segments preferably have different orientations (horizontal, vertical, +/−45°).

The minimum shutter size will be the consideration that drives the density of emitting apertures. Shuttering the emission from portions of the device may be performed using a liquid crystal device to block the light or by attaching wires to the individual resonant patterns in the device to alter the electron density and, hence, the resonance of the SPs in the area local to the aperture in question, thereby controlling a pattern's emission.

By using the invention to create small illumination spot sizes, lithography employing surface plasmon enhanced illumination provides numerous advantages, including:

a. small spot size (10–50 nm) for enhanced resolution;

b. high light transmission fractions (15%);

c. no diffraction problems with masks as the critical dimensions and CDs are reduced d. more flexible range the light wavelengths can be used;

e. maskless production technology is compatible with rapid prototyping and low production volumes as well as high volume runs; and f. reduced complexity and cost.

Conclusion

It is to be understood that the specific embodiments and applications of the invention that have been described are merely illustrative applications of the principles of the invention. Numerous modifications may be made to the methods and apparatus described without departing from the true spirit and scope of the invention.

What is claimed is:

1. Apparatus for directing electromagnetic energy onto a target in a small area of illumination, said apparatus comprising, in combination, a source of electromagnetic radiation, a substantially planar light barrier interposed between side source and said target, said light barrier defining a first electrically conductive surface on the side of said barrier exposed to incident radiation from said source and further defining a second surface on the opposite side of said barrier, said second surface being positioned adjacent to said target, said first electrically conductive surface of said light barrier being formed by a layer of conductive metal having a thickness greater than the skin depth of said metal at the frequency of said electromagnetic radiation, and said light barrier further comprising a barrier material that is opaque to the transmission of said electromagnetic radiation, said barrier material being positioned between said layer of conductive metal and said second surface, said conductive metal and said barrier material having significantly different dielectric properties, one or more apertures through said light barrier, each of said apertures passing from said first surface to said second surface through said layer of conductive metal and through said barrier material, each of said apertures having a width in at least one dimension that is smaller than one wavelength of said electromagnetic radiation, wherein said barrier material confines the extent of the electronic excitation induced in said second surface to the portion of said second surface that is near each of said apertures.

2. Apparatus as set forth in claim 1 wherein said layer of conductive metal extends into the interior side walls of each of said apertures terminating at said second surface in a limited area in the vicinity of each of said apertures.

3. Apparatus as set forth in claim 1 wherein said target is an optical data storage medium.

4. Apparatus as set forth in claim 1 wherein said target is a sample placed between the objective lens of a microscope and said second surface.

5. Apparatus as set forth in claim 1 wherein said target is a photoresist, which is exposed by said electromagnetic radiation in a lithographic process.

6. Apparatus as set forth in claim 1 further including a confined annular conductive area at said second surface surrounding each of said apertures whereby surface excitations at said second surface are confined to the vicinity of each of said apertures.

7. Apparatus as set forth in claim 6 wherein a layer of conductive metal is positioned at said second surface and a groove is formed in said layer of conductive metal surrounding each of said apertures to define said confined conductive area.

8. Apparatus as set forth in claim 1 wherein said barrier material is a dielectric that exhibits a bandgap that is larger than the frequency of said electromagnetic radiation.

9. Apparatus as set forth in claim 8 wherein said electrically conductive surface is constructed of a layer of a first metal and wherein said barrier material is composed of a dielectric and a different metal characterized in that said conductive surface and said barrier material have substantially different resonances.

10. Apparatus as set forth in claim 1 wherein said electrically conductive surface is constructed of a layer of a first metal and wherein said barrier material is a different metal characterized in that said conductive surface and said barrier material have substantially different resonances.

11. Apparatus as set forth in claim 10 wherein said layer of conductive metal extends into the interior side walls of each of said apertures terminating at said second surface in a limited area in the vicinity of each of said apertures.

12. Apparatus as set forth in claim 10 further including a confined annular conductive area at said second surface surrounding each of said apertures whereby surface excitations at said second are surface confined to the vicinity of each of said apertures.

13. Apparatus as set forth in claim 12 wherein a layer of conductive metal is positioned at said second surface and a groove is formed in said layer of conductive metal surrounding each of said apertures to define said confined conductive area.

14. A device for directing small areas of illumination onto a target comprising, in combination, a source of electromagnetic radiation, a substantially planar dielectric light barrier positioned between said source and said target, said light barrier being opaque to said electromagnetic radiation and defining a first surface facing said source and a second surface facing said target, a layer of metal affixed to said first surface of said light barrier, and an array of one or more apertures passing through said layer of metal and said light barrier, each of said apertures having a width in at least one direction which is shorter than the wavelength of said electromagnetic radiation whereby the electronic excitation induced in said second surface by electromagnet radiation passing through said apertures is confined to the portion of said second surface that is near each of said apertures.

15. The device set forth in claim 14 wherein light barrier has a thickness on the order of 200 nm.

16. The device set forth in claim 14 wherein said light barrier is selected from a group of dielectric materials including germanium, silicon dioxide, silicon nitride, alumina, and chromia.

17. The device set forth in claim 14 wherein each of said one or more apertures has a width in at least one direction that is between 10 nm and the dimension defined by the Rayleigh criterion for said frequency of electromagnetic radiation.

18. The device set forth in claim 14 wherein said layer of metal has a thickness at least as large as the skin depth of said metal at the frequency of said electromagnetic radiation.

19. The device set forth in claim 14 wherein said metal is selected from a group consisting of gold, silver, aluminum, beryllium, rhenium osmium, potassium, rubidium, cesium, rhenium oxide, tungsten oxide, and copper.

20. The device set forth in claim 14 wherein each of said apertures in said array is a slit having a long dimension and a shorter width dimension, said shorter width dimension being smaller than the wavelength of said radiation.

21. The method of directing electromagnetic radiation from a source to a small area of illumination on a target, which comprises, in combination, the steps of:

interposing a radiation barrier between said source and said target, said radiation barrier comprising the combination of a substantially planar dielectric material that is opaque to said electromagnetic radiation defining a first surface closest to said source and an opposing surface closest to said target and a layer of electrically conductive metal covering said first surface, said radiation barrier having an array of apertures therethrough, each of said apertures passing through said layer of electrically conductive metal and through dielectric material to permit radiation to pass from said first surface to said opposing surface to excite only a confined annular area of said opposing surface surrounding each of said apertures, activating said source to direct said radiation from said source onto said layer of electrically conductive metal to induce surface excitations in said layer of metal, and positioning said aperture adjacent to said target such that electromagnetic energy passing through said aperture induces surface excitations at said opposing surface only in said confined annular area to illuminate said target with said small area of illumination.

22. The method of claim 21 wherein said material that is opaque to said electromagnetic radiation is a dielectric having a bandgap that is larger than the frequency of said electromagnetic radiation.

23. The method of claim 21 wherein said material that is opaque to said electromagnetic radiation is metallic material different from said electrically conductive metal and having a substantially different resonance.

* * * * *